US011585804B2

(12) United States Patent
Dechev et al.

(10) Patent No.: US 11,585,804 B2
(45) Date of Patent: Feb. 21, 2023

(54) URINALYSIS DEVICE AND TEST STRIP FOR HOME AND POINT OF CARE USE

(71) Applicant: YOUCOUNT INC., Vancouver (CA)

(72) Inventors: Nikolai Dechev, Victoria (CA); Teodora Dechev, North Vancouver (CA)

(73) Assignee: YOUCOUNT INC., Vancouver (CA)

(*) Notice: Subject to any disclaimer, the term of this patent is extended or adjusted under 35 U.S.C. 154(b) by 1133 days.

(21) Appl. No.: 16/166,052

(22) Filed: Oct. 19, 2018

(65) Prior Publication Data

US 2020/0124587 A1    Apr. 23, 2020

(51) Int. Cl.
*G01N 33/487* (2006.01)
*G01N 33/493* (2006.01)
(Continued)

(52) U.S. Cl.
CPC ..... *G01N 33/48785* (2013.01); *G01N 33/493* (2013.01); *G01N 33/6827* (2013.01); *G01N 33/70* (2013.01); *A61B 5/14507* (2013.01); *A61B 2562/0295* (2013.01); *G01N 21/272* (2013.01); *G01N 21/78* (2013.01)

(58) Field of Classification Search
CPC .......... A61B 2562/0295; A61B 5/0022; A61B 5/14507; A61B 5/1455; A61B 5/207; G01N 21/255; G01N 21/272; G01N 21/78; G01N 21/8483; G01N 2201/0627; G01N 33/48785; G01N 33/493; G01N 33/6827; G01N 33/70; G16H 10/20; G16H 10/40; G16H 10/60; G16H 40/63

USPC ........ 702/19, 22, 25, 28, 31, 32; 436/43, 46, 436/63, 164, 165, 169; 422/400–404, 422/420, 82.05, 560–561, 563
See application file for complete search history.

(56) References Cited

U.S. PATENT DOCUMENTS 4,125,372 A * 11/1978 Kawai ................ G01N 21/8483
436/95
4,755,058 A    7/1988 Shaffer
(Continued)

FOREIGN PATENT DOCUMENTS

| | | |
|---|---|---|
| GB | 2339615 B | 2/2000 |
| WO | 2005001444 A1 | 1/2005 |
| WO | 2009/063185 A1 | 5/2009 |

OTHER PUBLICATIONS https://www.meddeviceonline.com/doc/stanford-s-new-take-on-the-at-home-urinalysis-test-0001, May 23, 2016.
(Continued)

*Primary Examiner* — Maureen Wallenhorst

(57) ABSTRACT

An exemplary urinalysis device for non-clinical use is described as having: a housing; a touchscreen on the housing; a test strip holder, which is removably, slidably engaged with the housing; at least two light emitting diode (LED) light sources, housed in the housing and including a white LED and a red-blue-green (RBG) LED; a camera module housed in the housing, both the plurality of LEDs and the camera module directed to an illumination and detection zone; a timer system; and/or a computational system in electronic communication with the plurality of LEDs, the camera module and the timer system, the computational system including a processor and a memory. Related methods and systems also are described.

31 Claims, 10 Drawing Sheets

(51) Int. Cl.
  *G01N 33/68* (2006.01)
  *G01N 33/70* (2006.01)
  *G01N 21/78* (2006.01)
  *A61B 5/145* (2006.01)
  *G01N 21/27* (2006.01)

(56) References Cited

U.S. PATENT DOCUMENTS

| | | | |
|---|---|---|---|
| 4,775,058 A | 10/1988 | Yatsko | |
| 4,934,817 A * | 6/1990 | Gassenhuber | G01N 21/8483 422/68.1 |
| 5,518,689 A | 5/1996 | Dosmann | |
| 5,654,803 A | 8/1997 | Howard | |
| 5,877,863 A | 2/1999 | Ross | |
| 7,313,257 B2 * | 12/2007 | Roman | G01N 21/253 382/128 |
| 2009/0155921 A1 * | 6/2009 | Lu | G01N 21/8483 436/164 |
| 2011/0223673 A1 | 9/2011 | Profitt | |
| 2011/0275162 A1 | 11/2011 | Xie | |
| 2013/0267032 A1 | 10/2013 | Tsai et al. | |
| 2014/0028857 A1 | 1/2014 | Jasperse | |
| 2014/0349326 A1 | 11/2014 | Ingber | |
| 2015/0301031 A1 * | 10/2015 | Zin | H04W 4/80 436/164 |
| 2016/0195553 A1 * | 7/2016 | Wang | G01N 21/77 422/403 |
| 2018/0059027 A1 | 3/2018 | Chen | |
| 2018/0059129 A1 * | 3/2018 | Dewar | G01N 35/00871 |
| 2020/0386753 A1 * | 12/2020 | Somes | G01N 33/558 |

OTHER PUBLICATIONS

Written Opinion of the International Searching Authority dated Dec. 30, 2019 for International Patent Application No. PCT/CA2019/000149, 4 pages.

International Search Report dated Dec. 30, 2019 for International Patent Application No. PCT/CA2019/000149, 3 pages.

Extended Supplementary European Search Report and Opinion for European Patent App. No. EP3867633A1, dated May 7, 2022 (9 pages).

* cited by examiner

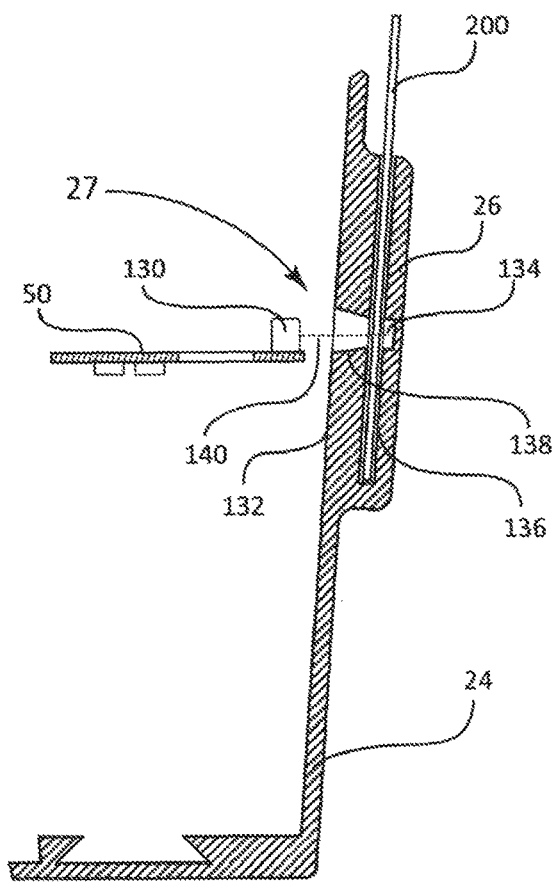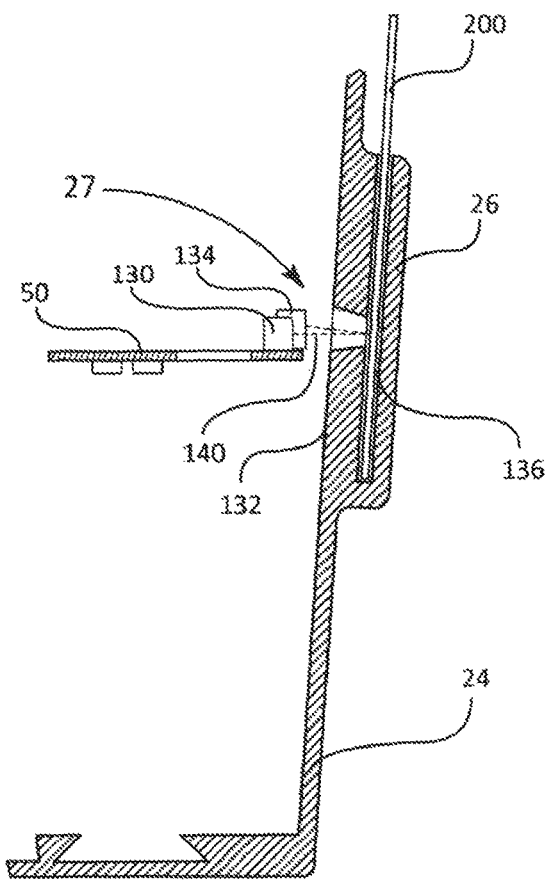

URINALYSIS DEVICE AND TEST STRIP FOR HOME AND POINT OF CARE USE

FIELD

The present technology is an easy to use urinalysis device with safeguards that make it suitable for home use. More specifically, it is a device that includes a timing mechanism to ensure that the sample is read within the required time frame for an accurate analysis, includes error checks for accurate analysis, and verifies the user qualifications and identity.

BACKGROUND

Most urinalysis devices are designed for clinical use only. In order to have an analysis done using the device, a prescription is needed. These devices are expensive, and are not suitable for home use, as they are designed for use by laboratory or medical technicians. These devices have laboratory-grade long menus that need to be followed accurately, they have limited or no data-logging capability, limited or no data-log retrieval/view capability, and they have little in the way of safeguards for use with non-professional users (i.e. home users or lay-users). If a user wishes to conduct an at home test, they usually only use a test strip (without electronic device) by visually comparing the test strip to a color chart that comes with the test strip. This introduces potential human error, both in terms of assessing the color on the strip in relation to the color on the chart, and also because the test is time sensitive.

Researchers at Stanford University have developed a device for in-home use that attempts to reduce human error (https://www.meddeviceonline.com/doc/stanford-s-new-take-on-the-at-home-urinalysis-test-0001). The device is a small black box into which both the urine sample and dipstick are inserted. A multi-layered loading system within the box ensures that the urine sample is distributed uniformly on the strip. A smartphone is used with the black box device, where the smartphone camera is used to film the reaction on the dipstick, and software on the smartphone notes specific times when the color is analyzed to ensure accurate timing for each separate pad. This system does prevent a test strip to be read and reported outside of the suitable timeframe for analysis. The light source is a white light source and therefore suffers the deficiency of a poor color spectrum.

United States Patent Application 20180059027 discloses a test strip analyzer. The test strip analyzer includes a frame, a test control module and an optical system. The test control module is disposed in the frame and includes a test strip carrier of a plurality of test strip carriers and a sample container of a plurality of sample containers. The test strip carrier is disposed on the frame and adapted to hold a test strip. The sample container is adapted to contain a sample. The optical system is disposed above the frame and the test control module and includes a light sensor and controller. The light sensor is configured to capture an image of the test strip. The controller is connected to the light sensor to control the light sensor, and the light sensor feedbacks the image to the controller. In addition, an analyzing method using the test strip analyzer is also provided. The light source is a white light source and therefore suffers the deficiency of a poor color spectrum.

United States Patent Application 20140349326 discloses an apparatus and method for analyzing a medical condition of a user. The apparatus may include a user interface configured to receive user identification information inputted by the user, an analyzer, and a processor all disposed within a common housing. The analyzer is configured to receive a biological specimen from the user and to analyze the biological specimen to generate analysis information. The processor is configured to store and forward the analysis information and to receive prescription information. The apparatus may include a communication device configured to transmit the user identification information and the analysis information to a doctor at a remote location for review and to receive the prescription information from the doctor. The apparatus then may dispense the prescribed medication or print a medication prescription. An image of the test strip is not recorded as a lens system to focus light onto a photodiode is used as the detector to record color level of individual sections of test strip. An ultraviolet light emitting diode is not contemplated, hence there is no measure of kidney disease.

United States Patent Application 20140028857 discloses a device including an optical reader, a first light source, and a second light source. The optical reader has a field of view comprising a first surface point and a second surface point horizontally offset from the first surface point along the field of view. The first light source is positioned a first distance from the first surface point. The first light source is operably connected to a first control channel and has a first luminous output. The second light source is positioned a second distance from the second surface point and has a second luminous output. The first distance is different from the second distance, and the first luminous output is different from the second luminous output such that the illumination at the first surface point is substantially equivalent to the illumination at the second surface point of the field of view. The light source is a white light source and therefore suffers the deficiency of a poor color spectrum.

United States Patent Application 20110275162 discloses low-cost assay test strip readers. Such readers enable creation of profiles of analyte reactions detected on an assay test strip utilizing a simple detector fixedly mounted to a body of the reader. The detector may be a single detector, such as a photodetector, which detects an optical signal at a single point. The assay test strip is inserted and/or removed from the test strip reader and the detector detects the optical elements of the strip during such insertion and/or removal. The movement of the test strip with respect to the body enables the detector to scan a length of the test strip, such that a one-dimensional profile of the optical signals can be generated. The reader may convert the detected profile into a displayable indication of analyte concentrations for diagnostic purposes. Moving the test strip relative to an array of detectors enables creation of a two-dimensional profile. The light source is a white light source and therefore suffers the deficiency of a poor color spectrum. An ultraviolet light emitting diode is not contemplated. A camera for capturing and recording an image is not provided.

U.S. Pat. No. 4,755,058 discloses a device for illuminating a surface and detecting the intensity of light emitted from the surface. The surface is directly illuminated by a plurality of light-emitting diodes disposed at an acute angle relative to the surface. Monochromatic light emitting diodes are used that are green, orange and red. An ultraviolet light emitting diode is not contemplated, hence there is no measure of kidney disease. An infrared light emitting diode is also not contemplated. A camera for capturing and recording an image is not provided.

U.S. Pat. No. 5,518,689 discloses a diffused light reflectance readhead in which one or more light-emitting diodes are used to illuminate a reagent pad. The light-emitting diode source is at an angle alpha with respect to the reagent pad, in order to reduce the specular reflection in relation to the reflected light received by the light sensor from the reagent pad. The light source is a white light source and therefore suffers the deficiency of a poor color spectrum. Further, a camera for capturing and recording an image is not provided.

U.S. Pat. No. 5,654,803 discloses an optical inspection machine for determining non-hemolyzed levels of occult blood in urine using reflectance spectroscopy. The apparatus is provided with a light bulb for successively illuminating a plurality of different portions of the reagent pad on which the body-fluid sample is disposed and a detector array for detecting light received from the reagent pad and generating a plurality of reflectance signals in response to light received from a corresponding one of the different portions of the reagent pad. The apparatus is also provided with means for determining whether the magnitude of one of the reflectance signals is substantially different than the magnitude of another of the reflectance signals. Where the body-fluid sample is urine, this capability allows the apparatus to detect the presence of non-hemolyzed in the urine sample. The light bulb may successively illuminate a plurality of overlapping portions of the reagent pad and may successively illuminate at least three different portions of the reagent pad which are linearly offset from each other. The light source is a white light source and therefore suffers the deficiency of a poor color spectrum. Further, a camera for capturing and recording an image is not provided.

U.S. Pat. No. 5,877,863 discloses an optical inspection machine for inspecting a liquid sample, such as urine, using reflectance spectroscopy. The machine includes a readhead for illuminating a target area substantially uniformly via only a single light-emitting diode and receiving light from the target area so that reagent tests may be performed. The readhead is provided with a housing, first and second light sources mounted in a fixed position relative to the housing, a light guide mounted to receive light from each of the light sources which conveys, when only one of the light sources is illuminated, substantially all of the light from the light source to illuminate a target area substantially uniformly, and a light detector coupled to receive light from the target area. Each of the first and second light sources is composed of only a single light-emitting diode for emitting substantially monochromatic light of a different wavelength. An ultraviolet light emitting diode is not contemplated, hence there is no measure of kidney disease. An infrared light emitting diode is also not contemplated. A camera for capturing and recording an image is not provided. There is no disclosure to the strip holder. The readhead includes divergent light guides which increase the cost of production.

What is needed is an easy to use, automated urinalysis device for home use. It should be inexpensive to manufacture and have as few parts as possible. It would be preferable if the device had an interactive touchscreen display and software that helps guide the home user through the test process and provides the home user with feedback about various possible test errors that may occur and provides suggestions to the user to take actions to prevent those test errors in future use. It would be preferable if the device included ultraviolet and infrared light emitting diode (LED) light sources, in addition to a white LED, an orange LED and red, blue, green (RBG) LEDs. It would be preferable if the test strip holder included a side on either side to allow a user to slide the test strip into the holder without worrying about it being loaded incorrectly. It would be still further preferable if it included at least one timer system that would inform the device computation system of the elapsed time between dipping and reading the test strip. Reading a test strip outside of the suitable timeframe leads to inaccurate results. It would be still more preferable if the device included digital storage to allow long-term data-logging, to thereby allow the user to review their urinalysis results over time. It would also be preferable if the data-log results could be displayed in graphs of test results vs time, combinations of graphs, and trend lines, on an interactive touchscreen display. It would be preferable if the device can save the long-term data-log onto a USB stick for backup or transfer. It would be preferable if the device can transmit the long-term data-log to an internet cloud server, for the user to access and review the graphs and results on remote computing devices. It would also be preferable if the test strip was specific to the device. It would be preferable if the test strip included a pad that retains chemicals that undergo a chemical reaction when exposed to water for the purpose of providing a measure of the time elapsed since the test strip was dipped in the urine sample, where the reaction is not affected by the other analytes present in urine. It would be still preferable if the device verified the user qualifications to use the device and verified the user identity.

SUMMARY

The present technology is an easy to use, automated urinalysis device for home use. It is inexpensive to manufacture and has as few parts as possible. It has an interactive touchscreen display and software that helps guide the home user through the test process and provides the home user with feedback about various possible test errors that may occur and provides suggestions to the user to take actions to prevent those test errors in future use. It includes ultraviolet and infrared light emitting diode (LED) light sources, in addition to a white LED, an orange LED and red, blue, green (RBG) LEDs. The test strip holder includes a side on either side to allow a user to slide the test strip into the holder without worrying about it being loaded incorrectly. It includes at least one timer system that informs the device computation system of the elapsed time between dipping and reading the test strip. Reading a test strip outside of the suitable timeframe leads to inaccurate results. The device includes digital storage to allow long-term data-logging, to thereby allow the user to review their urinalysis results over time. The device also allows data-log results to be displayed in graphs of test results vs time, combinations of graphs, and trend lines, on an interactive touchscreen display. The device can save the long-term data-log onto a USB stick for backup or transfer. The device can transmit the long-term data-log to an internet cloud server, for the user to access and review the graphs and results on remote computing devices. The test strip is specific to the device and is comprised of several (i.e. 8 to 12) reagent pad areas, which are absorbent material saturated with chemically active substance that undergo a color change in response to analytes in urine. Also, one of these pads provides a chemical reaction measure of the time elapsed since the test strip was dipped in the wet urine sample, where the reaction time is not affected by the other analytes present in urine. The software is configured to verify the user identity and to verify the user qualifications to use the device.

In one embodiment, a urinalysis device for non-clinical use is provided, the device comprising: a housing defining an interior, the housing including a front, a back opposite the front, a top, a bottom opposite the top and a pair of sides between the front and the back and the top and the bottom, one of the pair of sides including an aperture extending between an ambient environment and the interior; a slide which extends from the aperture into the interior; a touchscreen on the housing; a test strip holder, which is removably, slidably engaged with the slide; at least two light emitting diode (LED) light sources, housed in the housing and including a white LED and a red-blue-green (RBG) LED; a camera module housed in the housing, both the plurality of LEDs and the camera module directed to an illumination and detection zone; a timer system; and a computational system, the computational system in electronic communication with the plurality of LEDs, the camera module and the timer system, the computational system including a processor and a memory.

In the device, the LEDs may include an ultraviolet (UV) LED.

In the device, the slide may include a distal stop and a pair of rails along a length of the slide for locating the test strip holder in the illumination and detection zone.

In the device, the test strip holder may include a base and a pair of sides extending upward therefrom, to define a slot, the slot for locating a test strip in the test strip holder.

In the device, the timer system may comprise a computational timer and the camera module, the computational timer in electronic communication with the camera module.

In the device, the memory may be configured to send instructions to the processor to provide guided menus to display on the touchscreen.

In the device, the memory may be configured to send instructions to the processor to determine whether a test is conducted within a time limit.

In the device, the memory may be configured to send instructions to the processor to provide an error report if the test is conducted outside the time limit.

In the device, the memory may be configured to send instructions to the processor to conduct error checks.

In the device, the memory may be configured to send instructions to the processor to send error reports for display on the touchscreen.

In the device, the error checks may include one or more of checking for: correct insertion of the test strip holder; correct insertion of a test strip; anomalous results; and correct wetting of a test strip.

In the device, the memory may be configured to send instructions to the processor to analyze a dataset.

In the device, the memory may be configured to send instructions to the processor to graph the dataset for display on the touchscreen.

In another embodiment, a urinalysis system is provided, the system comprising at least one test strip and a urinalysis device, the test strip including a plastic strip, absorbent reagent pads adhered to the plastic strip and a blank absorbent pad adhered to the plastic strip, the urinalysis device comprising: a housing; a touchscreen on the housing; a test strip holder, which is removably, slidably engaged with the housing; at least three light emitting diode (LED) light sources, housed in the housing and including a white LED, an ultraviolet (UV) LED and a red-blue-green (RBG) LED; a camera module housed in the housing, both the plurality of LEDs and the camera module directed to an illumination and detection zone; a timer system; and a computational system, the computational system in electronic communication with the plurality of LEDs, the camera module and the timer system, the computational system including a processor and a memory.

In the system, the device may further comprise a slide and a test strip holder, the slide extending from an ambient environment into the housing and the test strip holder in removable, slidable engagement with the slide.

In the system, the slide may include a distal stop and a pair of rails along a length of the slide for locating the test strip holder in the illumination and detection zone.

In the system, the test strip holder may include a base and a pair of sides extending upward therefrom, to define a slot, the slot for locating the test strip in the test strip holder.

In the system, the timer system may comprise a computational timer and the camera module, the computational timer in electronic communication with the camera module.

In the system, one of the absorbent reagent pads may be a timing reagent pad.

In yet another embodiment, method of conducting urinalysis is provided, the method comprising: a user selecting a urinalysis device, the device including a housing, a touchscreen on the housing, a test strip holder, which is removably, slidably engaged with the housing, at least two light emitting diode (LED) light sources, housed in the housing and including a white LED and a red-blue-green (RBG) LED, a camera module housed in the housing, both the plurality of LEDs and the camera module directed to an illumination and detection zone, a timer, and a computational system, the computational system in electronic communication with the plurality of LEDs, the camera module and the timer, the computational system including a processor and a memory; the user selecting a test strip; the user wetting the test strip with urine to provide a wetted test strip; the user inserting the wetted test strip into the test strip holder; the user inserting the test strip holder into the housing; the camera capturing a plurality of images of the wetted test strip; the computational system providing a plurality of results; and the touchscreen displaying the plurality of results.

The method may further comprise the device displaying guided menus on the touchscreen.

The method may further comprise the device conducting error checks.

The method may further comprise the device displaying error reports on the touchscreen.

In the method, the error checks may include one or more of checking for correct insertion of the test strip holder, correct insertion of a test strip, anomalous results, and correct wetting of a test strip.

The method may further comprise the device analyzing a dataset to provide an analyzed dataset.

The method may further comprise the device displaying the analyzed dataset on the touchscreen.

In the method, the analyzed dataset may be graphically displayed.

The method may further comprise the device determining whether the urinalysis is conducted within a time limit.

The method may further comprise the user inserting a dry test strip into the test strip holder, inserting the test strip holder into the housing and removing the test strip holder from the housing prior to wetting the dry test strip, thereby starting the timer.

In the method the user may enter a user name and a password and the device may verify the user's identity, prior to the user selecting a test strip.

In the method the user may answer a series of questions prior to the user selecting a test strip, to verify the user's qualifications to use the device.

FIGURES

FIG. 5A is a side view of an embodiment of part of the timer system of the device of FIG. 1; FIG. 5B is a side view of an alternative embodiment of part of the timer system of the device of FIG. 1.

DESCRIPTION

Figure 1:
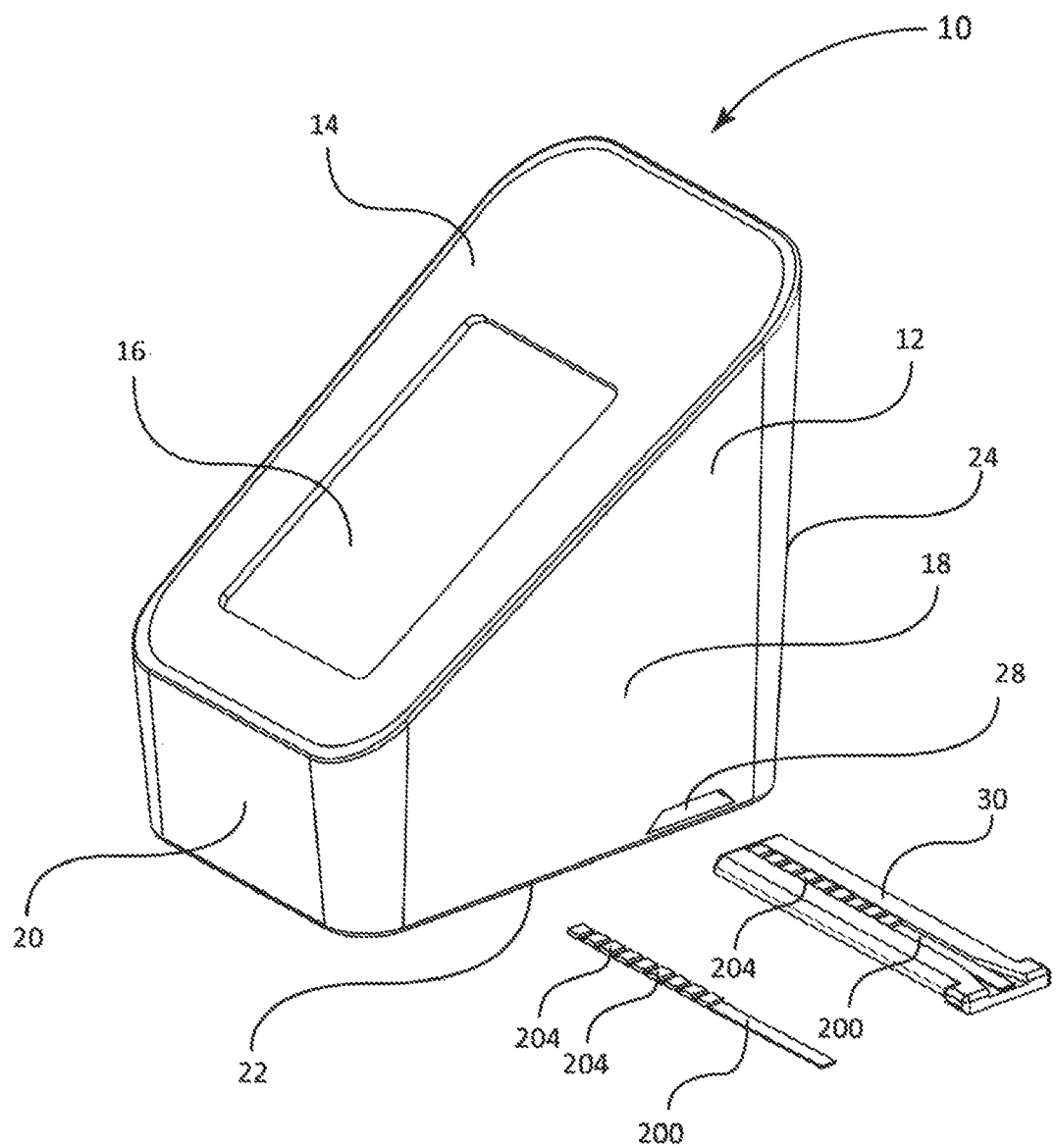
FIG. 1 is an isometric view of the device of the present technology.

Except as otherwise expressly provided, the following rules of interpretation apply to this specification (written description and claims): (a) all words used herein shall be construed to be of such gender or number (singular or plural) as the circumstances require; (b) the singular terms "a", "an", and "the", as used in the specification and the appended claims include plural references unless the context clearly dictates otherwise; (c) the antecedent term "about" applied to a recited range or value denotes an approximation within the deviation in the range or value known or expected in the art from the measurements method; (d) the words "herein", "hereby", "hereof", "hereto", "hereinbefore", and "hereinafter", and words of similar import, refer to this specification in its entirety and not to any particular paragraph, claim or other subdivision, unless otherwise specified; (e) descriptive headings are for convenience only and shall not control or affect the meaning or construction of any part of the specification; and (f) "or" and "any" are not exclusive and "include" and "including" are not limiting. Further, the terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. Where a specific range of values is provided, it is understood that each intervening value, to the tenth of the unit of the lower limit unless the context clearly dictates otherwise, between the upper and lower limit of that range and any other stated or intervening value in that stated range, is included therein. All smaller sub ranges are also included. The upper and lower limits of these smaller ranges are also included therein, subject to any specifically excluded limit in the stated range.

Unless defined otherwise, all technical and scientific terms used herein have the same meaning as commonly understood by one of ordinary skill in the relevant art. Although any methods and materials similar or equivalent to those described herein can also be used, the acceptable methods and materials are now described.

Definitions

Camera—in the context of the present technology, a camera is either a CMOS (Complimentary Metal Oxide Semiconductor) camera, or CCD (Charge Coupled Device) camera. Where the camera has n*m matrix of photosensors (example 1280×1024 photosensors, or other size). There can be two types of camera: a color camera or a monochromatic camera. A color camera records the R (Red), G (Green), and B (Blue) response from an image at its photosensors. Such a color camera may have a Bayer filter mosaic overlaid on its photosensors (i.e. a color filter array for arranging R, G, B color filters at select locations on a square grid of photosensors) or other filter mosaic. Alternatively, a monochromatic camera is a CMOS or CCD camera of n*m photosensors with no color filters on the photosensors, where the photosensors are sensitive to any incoming light from approximately 900 nm to 350 nm.

Timer system—in the context of the present technology, the timer system is any combination of components which start a timer prior to or immediately after the test strip is placed in the wet urine sample. The timer system informs the device computation system how much time has elapsed between immersion of the test strip in a wet urine sample and reading the test strip. Reading a test strip outside of the suitable timeframe leads to inaccurate results.

DETAILED DESCRIPTION

Figure 2:
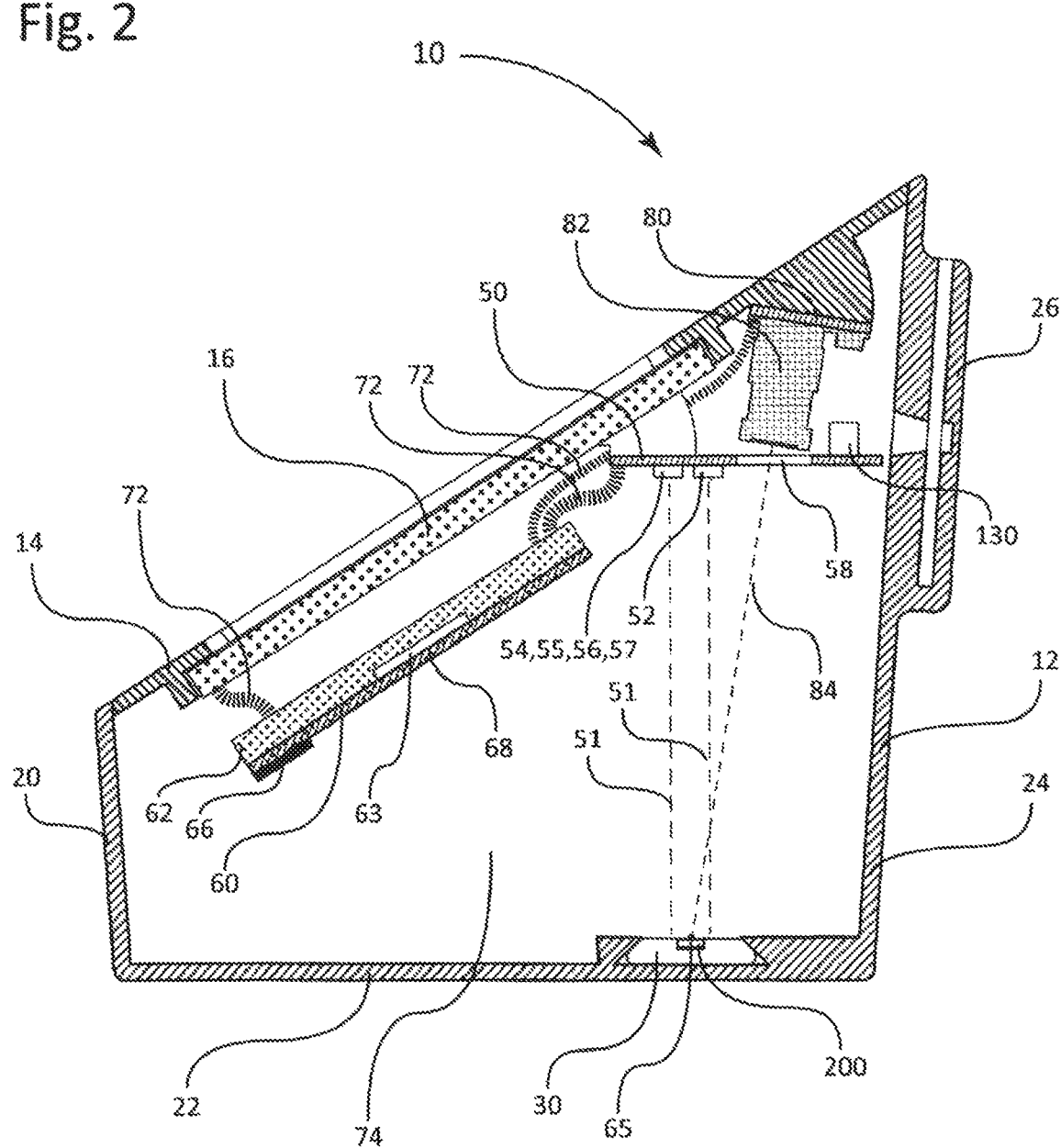
FIG. 2 is a longitudinal sectional view of the device of FIG. 1.

A urinalysis device, generally referred to as 10 is shown in FIG. 1. The device 10 has a housing 12, which is preferably an injection molded plastic polymer, such as, but not limited to acrylonitrile butadiene styrene (ABS). It has a top panel 14 with a color touchscreen 16, two sides 18, a front 20, a bottom 22 and a back 24. As shown in FIG. 2, the back 24 has a test strip retainer 26 either attached to it, or continuous with it. Returning to FIG. 1, an aperture 28 in one side 18 is sized to releasably accept a test strip holder 30. The test strip holder 30 is made of injection molded ABS. The test strip holder 30 releasably retains a test strip 200, which has several (i.e. 8-12) reagent pads 204. It is also shown alone.

As shown in FIG. 2, there are three printed circuit boards (PCBs) 50, 60, 80. The illumination PCB 50 holds the LEDs, which are at least one RGB LED 52 (Red of 620 to 660 nm, Green of 520 to 540 nm and Blue of 460 to 480 nm), at least one white LED 54, at least one orange LED 55 of 605 to 606 nm, at least one infrared LED 56 of 850 to 950 nm and at least one ultraviolet (UV) LED 57 of 385 to 405 nm. The LEDs provide illumination of the test strip 200 and are positioned such that their optical axis 51 is close to the middle of the test strip holder 30 longitudinal axis 65 (and therefore the longitudinal axis of the test strip 200 when in place). The device 10 also holds the computation system 62 which includes a Raspberry® Pi 3B processor 63 running a Linux operating system 64, and a 16 Giga byte (GB) Secure Digital (SD) memory card 66. A timer 68 is either in the processor 63 or is a separate unit in electronic communication with the processor 63. The illumination PCB 50 is in electronic communication with the computation system 62, and the touch screen 16 is in electronic communication with the computation system 62. Both are in electrical communication with the power source 70, which may be batteries or an electrical connection for plugging into an outlet. The detection PCB 80 holds either a color camera module 82 with a lens or a monochromatic camera module 82 with a lens. It is in electronic communication with the computation system 62 and in electrical communication with the power source 70. The illumination PCB 50 has a circular camera aperture 58 through which the camera has an optical line-of-sight 84 to the test strip 200 in the test strip holder 30. The PCBs 50, 60, 80 and the electrical connections 72 are housed in the interior 74 of the housing 12.

The device includes a UV LED 57 for illuminating a blank reagent pad 212 (see FIG. 8 for the test strip 200) for measuring cell-free nucleic acids. The blank reagent pad is like all the other pads, in that it is made of a fluid absorbing material. Cell-free nucleic acids in urine are potential biomarkers of kidney disease, hence being able to measure these is a significant improvement over existing testing devices and test strips.

Figure 3:
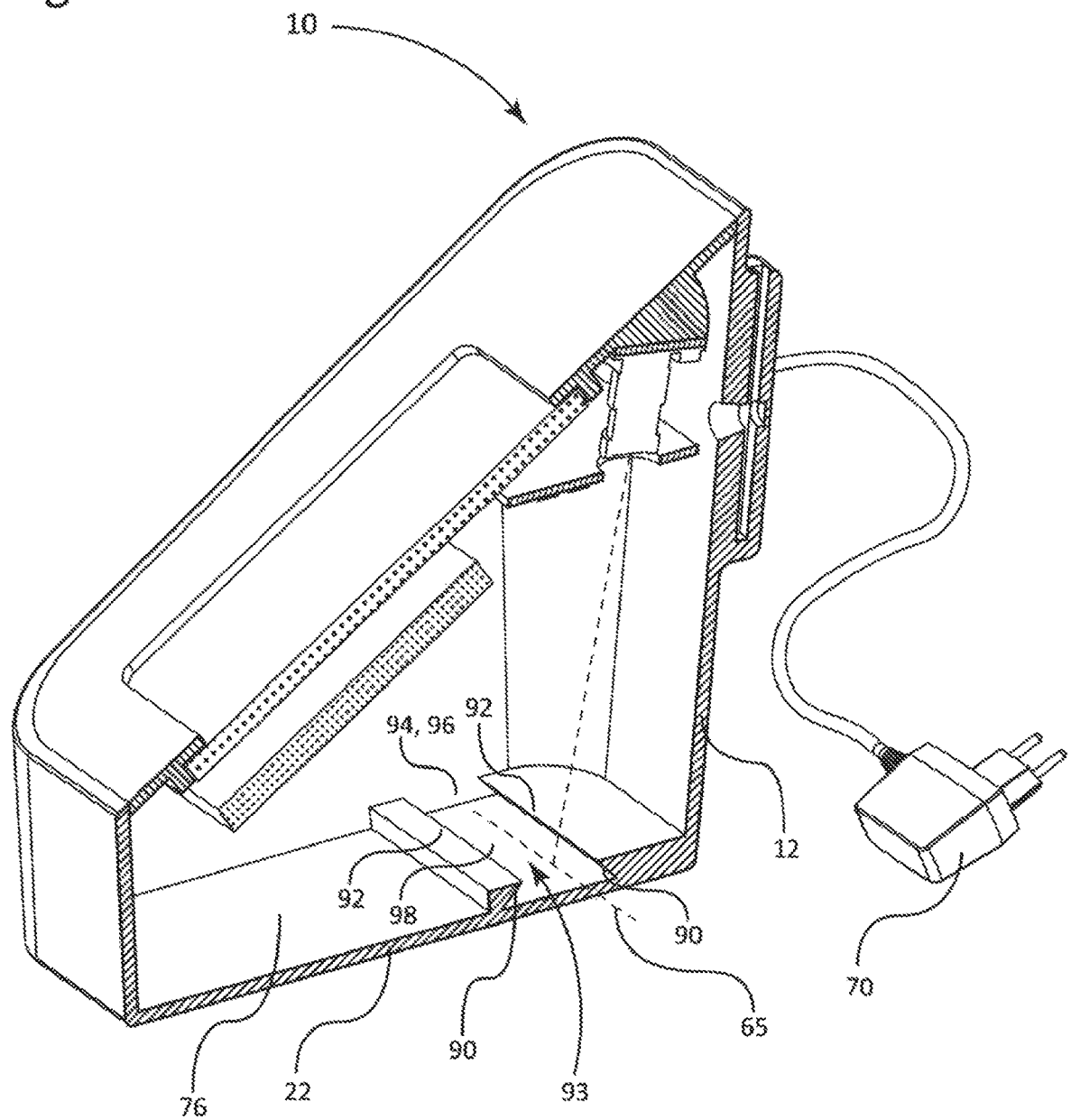
FIG. 3 is an isometric sectional view of the device of FIG. 1.

As shown in FIG. 3, the inner surface 76 of the bottom 22 of the housing 12 has a slide 98. The slide 98 is sized to slidably accept the test strip holder 30. The slide 98 has a rail 90 on either side 92 and a stop 94, which is the inner surface of the side 18 at the distal end 96 of the slide 98 to ensure that the test strip holder 30 is properly located in the illumination and detection zone, generally referred to as 93.

Figure 4:
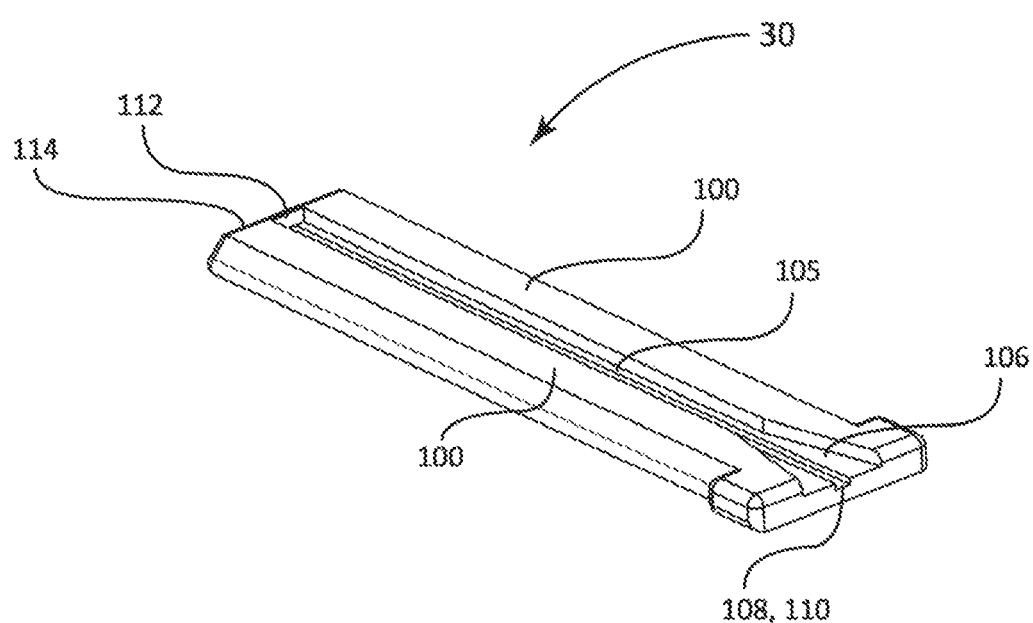
FIG. 4 is an isometric view of the test strip holder of the device of FIG. 1.

As shown in FIG. 4, the test strip holder 30 includes two sides 100, one on either side, to define a slot 105. The sides 100 allow the test strip 200 to be slid between the base 106 and the sides 100, in the slot 105, ensuring that the test strip 200 is properly loaded on the test strip holder 30. A gutter 108 is located in the base 106. The gutter 108 is included to collect any urine that may not have been properly blotted from the test strip 200. The gutter 108 may hold an absorbent lining 110. The test strip holder 30 has a stop 112 at the distal end 114 to ensure the test strip 200 is properly located in the test strip holder 30.

As shown in FIG. 5A, the test strip retainer 26 is part of the timer system 27. The timer system 27 includes a LED light source 130, the detector 134 and the timer 68. The LED light source 130 is preferably either a laser LED source, or an infrared LED source, or a visible light LED source, and the detector 134 is preferably a photodiode, or phototransistor, or a camera module. The LED source 130 and detector 134 are located in a way as to detect the correct alignment between the test strip retainer 26 and the test strip 200. The LED source 130 is in electrical communication with the power source 70 and is turned on when triggered by the software on the computation system 62. The detector 134 is in electronic communication with the computation system 62 and timer 68. In one embodiment, the LED source 130 and detector 134 are arranged in a photo interrupter arrangement, where the LED source 130 is on a PCB 50 near a first inner surface 132 and the detector 134 is located on an opposite inner surface 136. The LED source 130 is aligned with the via an LED aperture 138. The dry (undipped) test strip 200 is located between the LED source 130 and the detector 134 such that the light beam 140 is normally broken but becomes continuous by the removal of the test strip 200. Upon removal, the timer is started. This prevents reading a test strip 200 outside of the suitable time frame and therefore prevents inaccurate readings caused by reading the test strip 200 outside of the suitable time frame.

In an alternate embodiment shown in FIG. 5B, the LED source 130 and detector 134 are arranged in a proximity sensor arrangement, where the LED source 130 is on a PCB 50 near an inner surface 132 and the detector 134 is located on the same PCB 50 or adjacent inner surface 132. The dry (undipped) test strip 200 is located close to both the LED source 130 and the detector 134 such that the light beam 140 from the LED source 130 shines onto and reflects from the test strip 200. The intensity of the reflected light is measured by the detector 134, to indicate the presence of the test strip 200 in the test strip retainer 26. Upon removal of the test strip 200, the timer is started. This prevents reading a test strip 200 outside of the suitable time frame and therefore prevents inaccurate readings caused by reading the test strip 200 outside of the suitable time frame.

Figure 6:
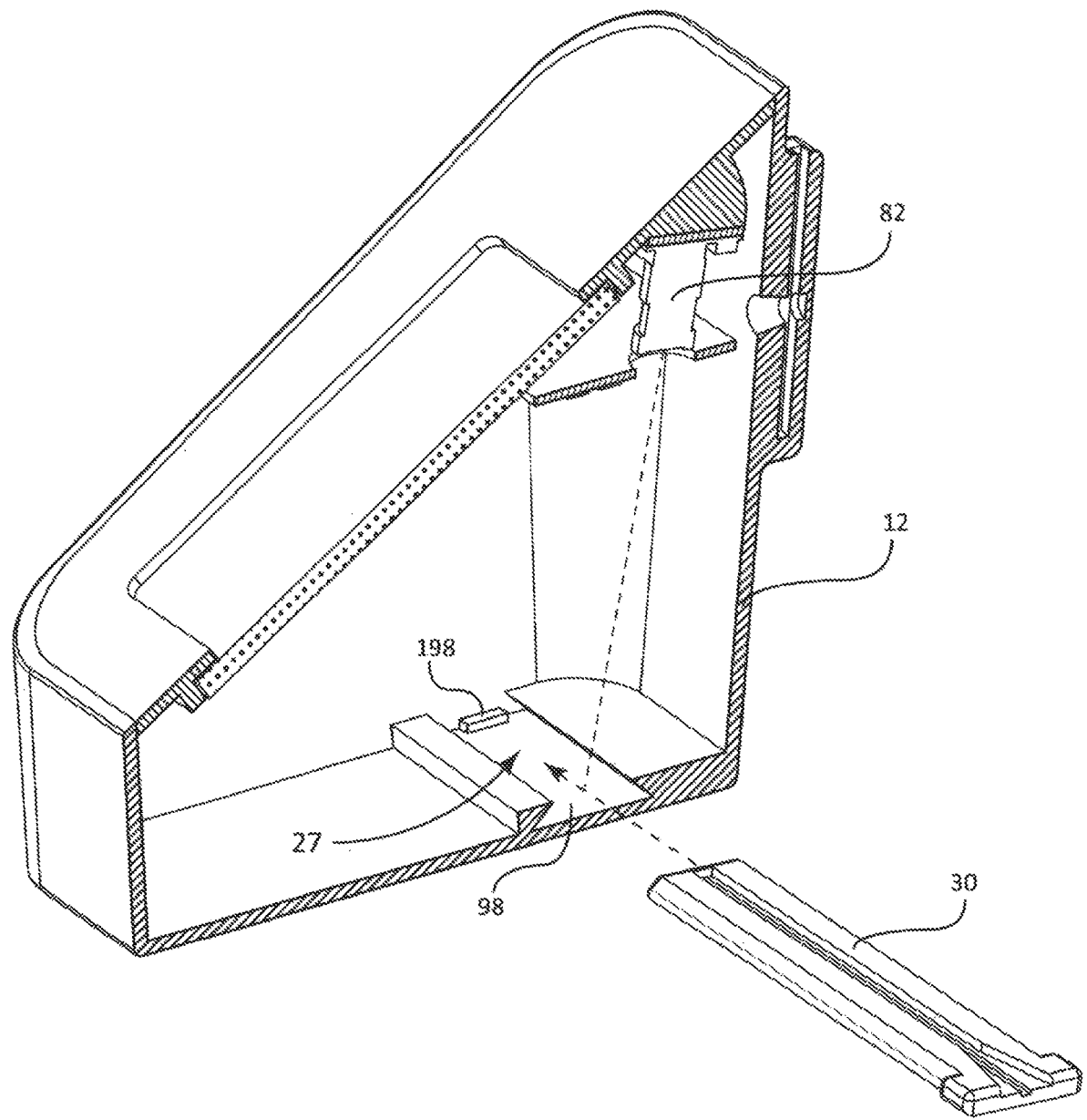
FIG. 6 is an isometric sectional view of another embodiment of part of the timer system of the device of FIG. 1.

As shown in FIG. 6, in an alternative embodiment, the timer system 27 is a mechanical system. It includes a test strip holder 30, a switch 198, the timer 68 and a dry (undipped) test strip 200. The dry (undipped) test strip 200 is inserted into the test strip holder 30, which is in turn inserted into the slide 98, prior to running the test. The camera module 82 verifies that a clean dry strip 200 is loaded into the test strip holder 30 and that the test strip holder 30 is inserted all the way in the slide 98, thereby depressing the switch 198. When the user withdraws the test strip holder 30 from the slide 98, the switch 198 is triggered and the software timer begins. The user then has a finite amount of time to remove the test strip 200 from the test strip holder 30, to dip the test strip 200 in the urine sample, to load the test strip 200 into the test strip holder 30, and to insert the test strip holder 30 into the slide 98. Upon re-insertion of the test strip holder 30 fully into the slide 98, the switch 198 is again triggered and the elapsed time is noted by the computation system 62. This prevents reading a test strip 200 outside of the suitable time frame and therefore prevents inaccurate readings caused by reading the test strip 200 outside of the suitable time frame.

Figure 7:
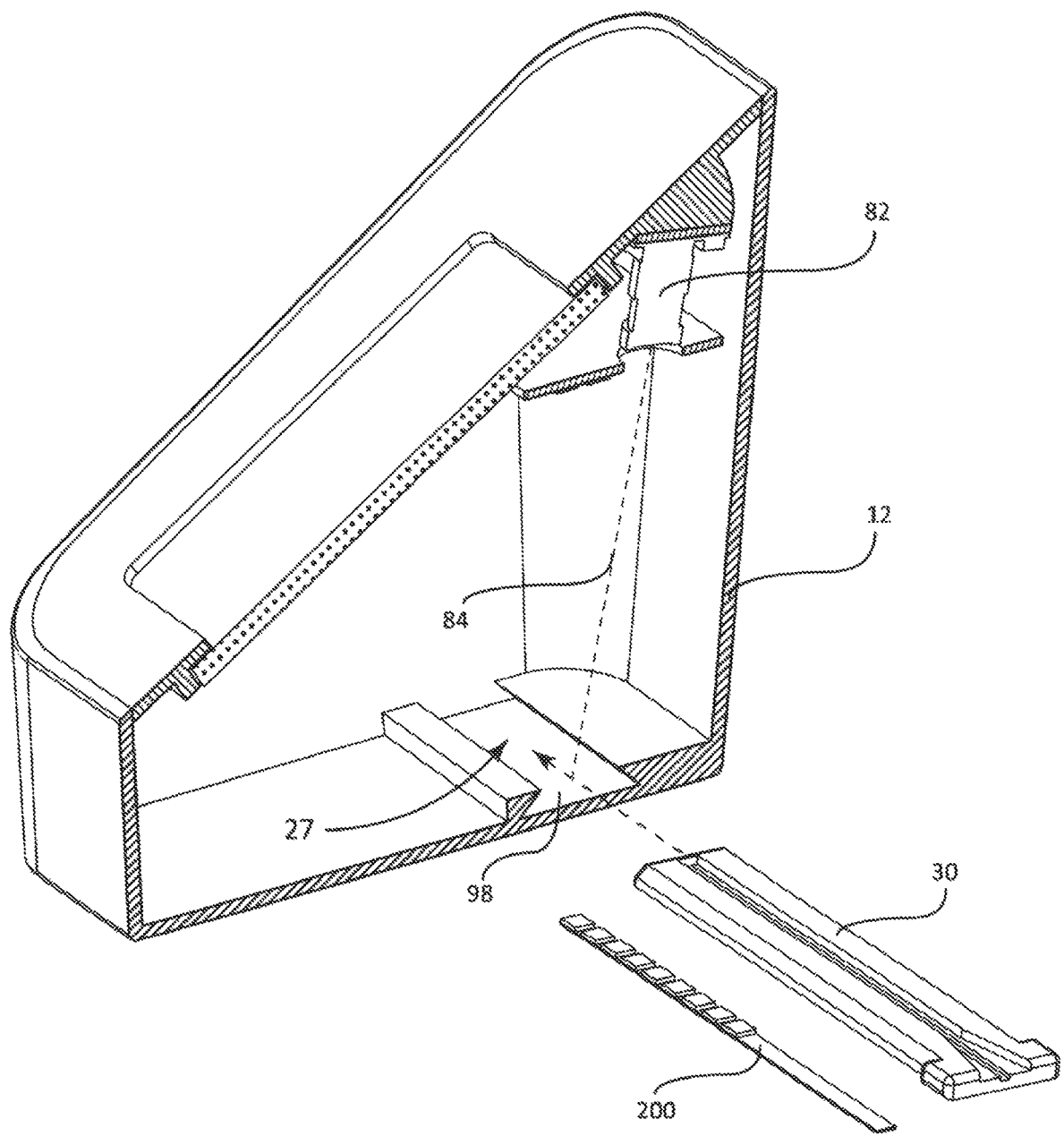
FIG. 7 is an isometric sectional view of another embodiment of part of the timer system of the device of FIG. 1.

As shown in FIG. 7, in an alternative embodiment, the timer system 27 consists of the camera module 82 and the timer 68. A dry (undipped) test strip 200 is inserted into the test strip holder 30, which is in turn inserted into the aperture 28, prior to running the test. The camera module 82 verifies that a clean dry strip 200 is loaded into the test strip holder 30, and that the test strip holder 30 is inserted all the way in the slide 98. The camera 82 has a line of sight 84 and continuously records and processes images of the test strip holder 30, such that when the user withdraws the test strip holder 30 from the slide 98, the camera module 82 detects the withdrawal and the software timer begins. The user then has a finite amount of time to remove the test strip 200 from the test strip holder 30, to dip the test strip 200 in the urine sample, to load the test strip 200 into the test strip holder 30, and to insert the test strip holder 30 into the slide 98. Upon re-insertion of the test strip holder 30 fully into the slide 98, the camera module 82 detects the re-insertion, and the elapsed time is noted by the computation system 62. This prevents reading a test strip 200 outside of the suitable time frame and therefore prevents inaccurate readings caused by reading the test strip 200 outside of the suitable time frame.

Figure 8:
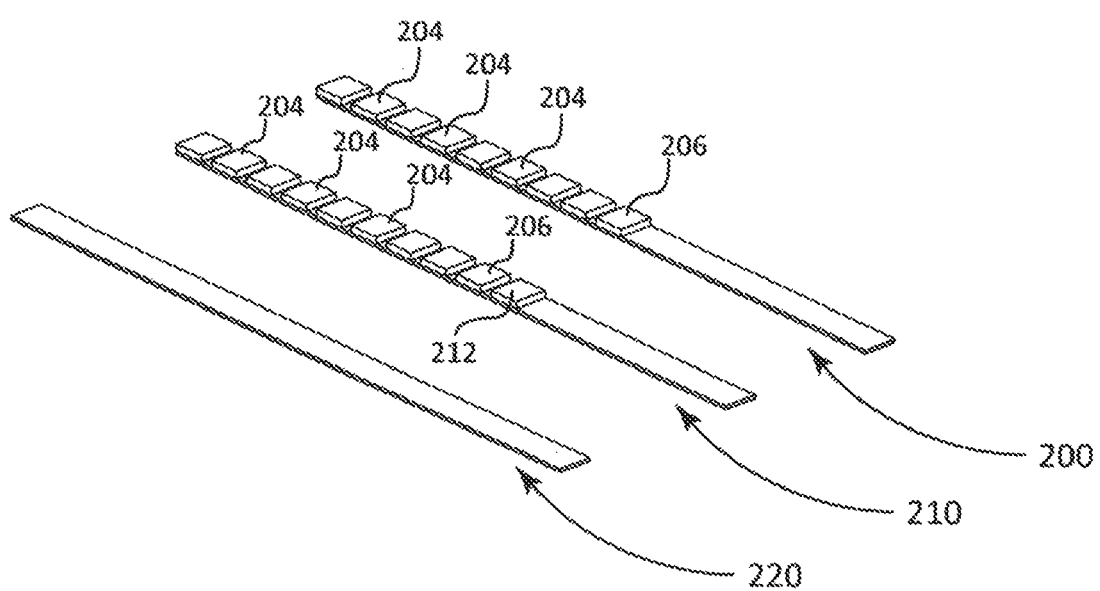
FIG. 8 is an isometric view of the test strips and blank strip of the present technology.

As shown in FIG. 8, in an alternative embodiment, the timer system 27 is the timer 68, the camera module 82 and a chemically active substance on a reagent pad 206, which is called a timing reagent pad 206, which is included on the test strip 200. This timing reagent pad 206 undergoes a color change in response to contact with water. The timing reagent pad 206 is designed to have a slow-reaction, such that its color change from the first second of immersion in the wet urine sample, to the $60^{th}$ second after the initial immersion, produces a gradual change of color, where the color change can be read by the camera module 82 and resolved into time steps of 1-2 seconds. The color change may be from pink to blue, or any other color resolvable by the camera module 82. The color change allows for the measure of the time elapsed since the wet test strip 200 was dipped in the wet urine sample and is noted by the computation system. The chemical reaction creating the color change is not affected by the other analytes present in the urine sample, and hence provides an accurate measure of time independent of the chemistry of the urine. This prevents reading a test strip 200 outside of the suitable time frame and therefore prevents inaccurate readings caused by reading the test strip 200 outside of the suitable time frame.

The test strip 200 has 9 or 8-12 or more reagent pads 204, which are absorbent material saturated with chemically active substances, which are dried and affixed to the plastic strip with double-sided adhesive. The chemically active substances undergo a color change in response to analytes in urine. These analytes may be one or more of, but not limited to: protein; bilirubin; ketones; leukocytes; nitrite; pH; creatinine; calcium; microalbumin; gonadotropin; follicle stimulating hormone; lutenizing hormone; estrogen; cell-free nucleic acids; specific gravity; urobilinogen; ascorbic acid; glucose; and occult blood. The inclusion of an ascorbic acid test pad in addition to the specific gravity test pad ensures that only valid test results will be displayed. A high ascorbic acid level in the urine leads to test inaccuracy, hence, should a high content be recorded, the device will indicate an invalid reading.

As shown in FIG. 8, in an alternative embodiment, the test strip 210 has 9 or 8-12 reagent pads 204 and a blank non-reactive pad 212. The blank serves a dual purpose for LED source color calibration and does not undergo a color change when wet or dry. Accordingly, when illuminated with a white LED light source 54, there will be a corresponding white light reflection, to be used for calibration. When illuminated with a blue LED light source, there will be a corresponding blue light reflection, to be used for calibration. When illuminated with a green LED light source, there will be a corresponding green light reflection, to be used for calibration. When illuminated with a red LED light source, there will be a corresponding red light reflection, to be used for calibration. When illuminated with the UV LED 57, the presence of fluorescence will be indicative of nucleic acids in the urine, as described above.

The software consists of two integrated portions, which are the front-end Graphical User Interface (GUI), and the back-end operations code (OC). The GUI takes inputs from the user, verifies the user identity, verifies the user qualifications, guides the user to operate the device, provides the user with feedback, provides the user with general knowledge of urinalysis, and also provides graphing/charting information regarding past test results. The OC performs various operations such as: controlling the Timer, controlling the LED illumination system, controlling the Camera Module to take images of the test strip 200, 210, analyzing images of the test strips 200, 210 for possible errors or anomalous results, analyzing images of the test strips 200, 210 to obtain colorimetric test results, calibration and mapping of the test results, recording test results to system memory, retrieving test results from the system memory, saving the test results data-log onto a USB stick for data backup, transmitting the test results data-log to an internet cloud server, calibrating the device, and coordinating between OC operations and the GUI. As the device 10 is intended for home use, the software (GUI and OC working together) includes a number of usability features to ensure device performance and effectiveness in the home.

A high-level software flowchart of the major operations is shown in FIG. 8. The GUI takes input from the user via the touchscreen 16, and the home user can navigate through various operations available. When the device 10 is connected to a power source it enters the Power Up & Initialize Hardware 300 mode, where it boots the embedded system, starts the main application, and initializes the electronic hardware. It then enters the Start Screen 302 mode, where it waits for user input to perform at least four possible operations. One possible operation is the Interactive Training & Instruction Manual 304, which provides the home user with instruction and training information in the form of text, graphics, and videos to train the user in operating the device 10. Another possible operation is the Create New User 306 whereby a user creates a new account profile, creates a password, enters personal information, declares intended use of the device, and declares health information. The user first identifies themselves in the device with their name, device password, email address, age, gender, height, weight and similar data. Next, this operation will prompt the home user to declare their intended use of the device, including use for, but not limited to: part of an athletic program; part of a fitness-orientated program; part of a bodybuilding program; part of a diet and nutritional program; fertility or ovulation monitoring; general interest, asymptomatic (i.e. healthy) person use; menopause hormone monitoring; sexually transmitted disease; recreational drug use; illicit drug use; urinary tract infection; monitoring kidney function; monitoring liver function; dehydration; and monitoring glucose levels. Next, operation 306 goes to another screen, where the device prompts the home user to answer a set of qualification questions as follows. The first question is, "Please make a declaration about your current state of health" (wherein the home user will select from healthy/unhealthy). The device will prompt the home user to complete a declaration about their current state of health, by asking questions including, but not limited to, "Do you currently have any of the following conditions?". A series of check-boxes are displayed listing conditions such as, but not limited to heart conditions, cancer, diabetes, kidney problems, liver problems, etc. Next another question will ask "Are you taking any medications for any of those health conditions?". Next, the device will prompt the home user to complete a declaration about their recent health history, by asking questions such as, but not limited to "Have you had any of the following conditions in the past 12 months?" A series of check-boxes are displayed listing conditions, such as, but not limited to: stroke; heart attack; etc. The home user is then prompted to confirm their answers, and the device then performs a health qualification check of the user based on their intended use of the device and their health information to say, "Yes, you are qualified to use this device for this purpose", or "Sorry, given your health condition(s) you do not qualify to use the device for this purpose". Based on the outcome of the health qualification check, software then performs the Create User Account and Data File 308 operation, whereby that new user's account and data file for their intended use is created and stored in a data file. Another possible operation is the Quit and Power Down 314 operation, which will close the electronic hardware resources, close the main application, and power down the embedded system. Another possible operation is the Login Existing User 310 operation, whereby an existing user with a previously created account logs into the system using their username and password, the system verifies the intended user, after which the software performs the Load User Account Info and Data File 312 operation, which will load the user account information into active memory and load the user test results data-log into active memory. Following operation 312, the software will enter the Main Application Screen 316 operation, where it will wait for user input to perform at least five possible operations.

Figure 9:
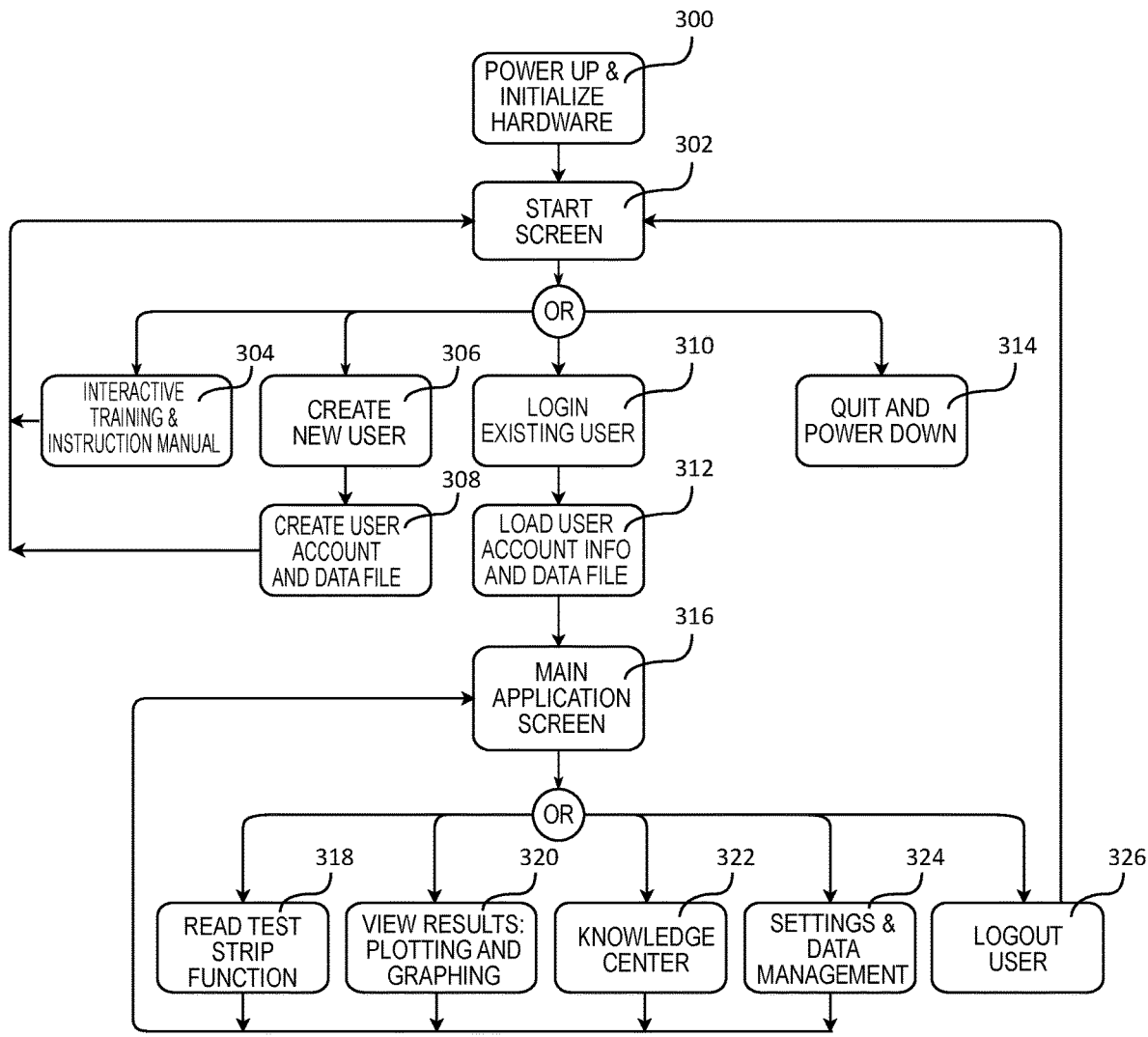
FIG. 9 is a flow chart of the operation of the device of FIG. 1.
Figure 10:
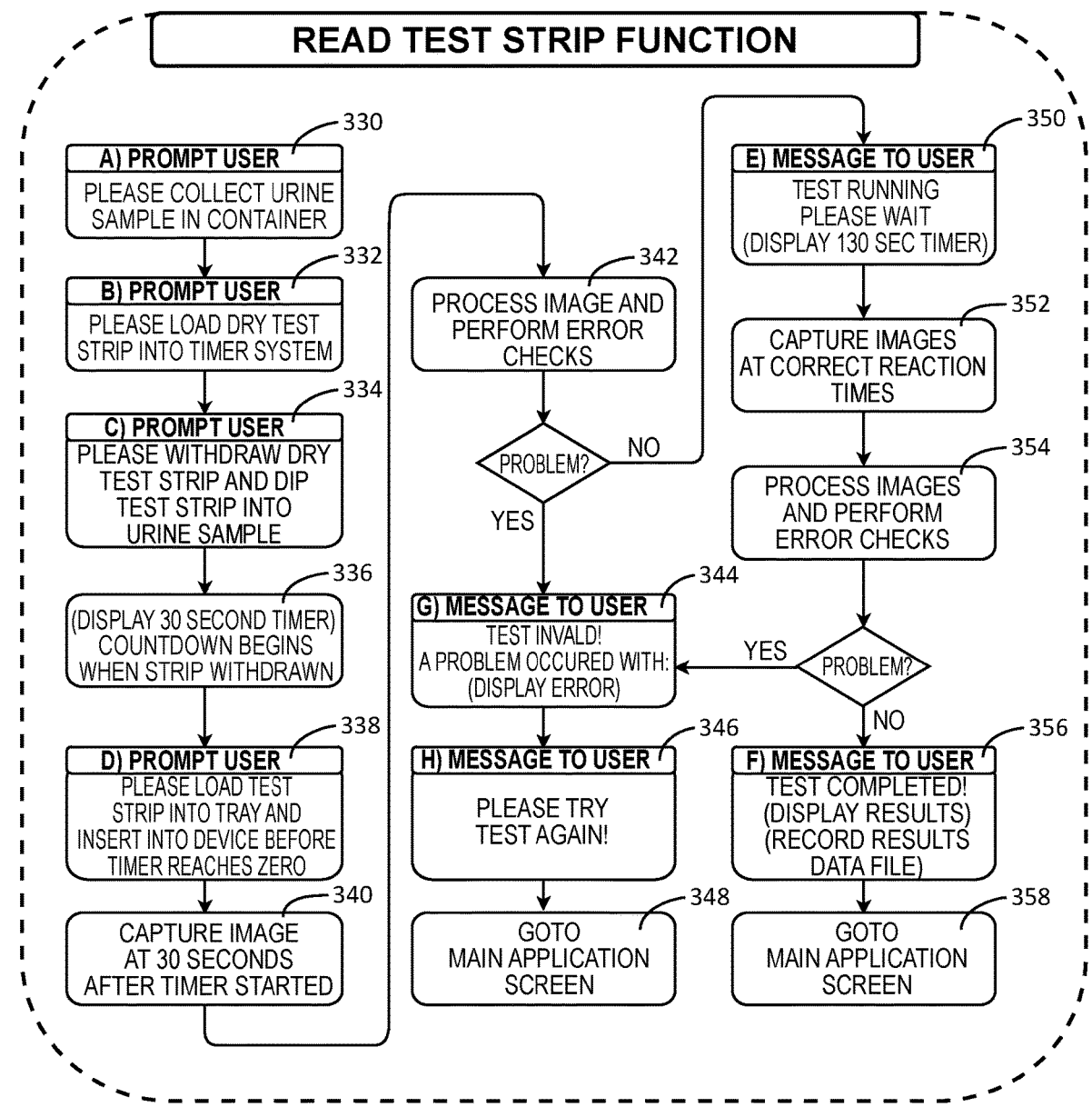
FIG. 10 is flow chart of the "Read test Strip Function" of the device of FIG. 1.

From the Main Application Screen 316, one possible operation branch is the Read Test Strip Function 318, which includes several sub-operations, as illustrated in FIG. 10. Continuing in FIG. 9 From the Main Application Screen 316, another possible operation branch is the View Results: Plotting and Graphing 320, which allows the user to review their past test results data-log. Past test results data-log can be viewed in either visual graphs, or numeric text results. For visual graphs, the user is presented with an interactive graph screen whereby they select their urine analyte(s) results of interest such as protein; bilirubin; ketones; leukocytes; nitrite; pH; cell-free nucleic acids; specific gravity; urobilinogen; ascorbic acid; glucose; and occult blood, or any combination thereof. Additionally, they select the date range to plot the urine analyte(s) results over time, which can be 1 week; 1 month; 3 months; 6 months; 1 year, or any custom date range they specify. Additionally, they can use the touchscreen with a two-finger pinch motion or two-finger expand motion, to interactively zoom out and zoom into the graph, respectively. This allows for zoom out/in of the vertical axis which displays the analyte levels and zoom out/in of the horizontal axis which displays the date range. The user can also use a swipe motion on the touchscreen to scroll through the different urine analytes one at a time. The user can change graph settings to display the result data levels with a linear scale, or a logarithmic scale, or use a custom vertical scale range. All result data can be displayed with indicators for measurement uncertainty (i.e. error bars), such as high and low bars above and below the data point, candlestick bars, thick lines that encompass the high and low uncertainty, or other common uncertainty indicators. The user can use the touchscreen to place trend and indicator tools such as linear regression lines, quadratic regression lines, cubic regression lines, ordinary user defined lines, points, stars, and text. The user can capture a screenshot of their result data at any time, which is saved to a file in a common format (.PNG, .JPEG, .SVG, etc.) suitable for personal review, electronically sharing with others, or printing via a printer. When the user is finished using View Results: Plotting and Graphing 320, they can return to the Main Application Screen 316.

From the Main Application Screen 316, another possible operation branch is the Knowledge_Center 322, which allows the user to learn about various aspects of urinalysis, where such information is normally available from health journals, health books, or other health literature. All sources of information are referenced. This information is provided by text, images, animations, video, or any combination thereof, to communicate topics such as information about each urine analyte and its relation to human health, information regarding a plurality of analyte measurements in relation to human health, and limitations on interpreting analyte measurements. Human health information means medical health information, physical health (fitness or body building) information, fertility information, or other health aspects. Additionally, all the Interactive Training and Instruction Manual 304 information is available for access within the Knowledge Center 322. When the user is finished using Knowledge Center 322, they can return to the Main Application Screen 316.

From the Main Application Screen 316, another possible operation branch is the Settings and Data Management 324, which allows the user to perform a number of operations, as follows: (a) User Settings Menu, which allows the user to review and edit their user account information; (b) User Data Menu, which allows the user to review their test result data-log in text format in whole, in portions, or by individual test, to delete their test result data-log in whole, in portions, or by individual test or to add or edit notes to their test result data-log by individual test; (c) User Data Backup Menu, which allows the user to save their test result data-log in whole, in portions, or by individual test to a backup device (USB memory stick, USB memory drive, or similar) connected to the USB port on the device 10. The test result data-log will be saved in a comma separated value (.csv) file, or other standard data file, which can be imported into other computing platforms or computing software. It also allows the user to save any captured screenshots from the View Results: Plotting and Graphing 320 operation (d) User Cloud Server Menu, which allows the user to upload their test result data-log in whole, in portions, or by individual test to a cloud server on the internet, connected via WiFi connectivity on the device 10. The test result data-log will be uploaded in a comma separated value (.csv) file, or other standard data file, which can be imported into other computing platforms or computing software. Also, it allows the user to upload any captured screenshots from the View Results: Plotting and Graphing 320 operation. It also provides settings for periodic automatic upload of test result data-log to the cloud server; (e) User Internet Menu which allows the user to establish a WiFi internet connection and adjust connection password and settings; (f) Calibration Menu, which allows the user to calibrate the device 10 as described later; (g) Test Strip Menu, which allows the user to test dry (undipped) test strips 200, to ensure they are still viable. Dry (undipped) test strips 200 which are properly stored in dry conditions with a desiccant in their container have a specific colorimetric response within a narrow color range, which can be measured by the device 10. If the dry (undipped) test strips 200 produce a result outside this range, the device 10 will inform the user that the dry (undipped) test strips 200 are spoiled and should not be used. When the user is finished using Settings and Data Management 324, they can return to the Main Application Screen 316.

From the Main Application Screen 316, another possible operation branch is the Logout User 326 operation, which allows the user to logout of their account, and returns the device 10 to the Start Screen 302 operation. When a user is logged out, no one can access their account, their test result data-log, or personal information, which allows for data security.

As shown in FIG. 10, when selected by the user, the Read Test Strip Function begins with a Prompt User 330 operation, which guides the user to collect a urine sample into a container prior to conducting the test. The guiding is done by text, graphics, animations, audio, video, or any combination thereof, to easily communicate to the user as to how to perform the required step. Next, Prompt User 332 guides the user to load a dry (undipped) test strip 200 (which in all instances can be test strip 210) into the timer system 27 or to remove the test strip 200 from the test strip retainer 26 of the timer system 27. Next, Prompt User 334 guides the user to withdraw the dry (undipped) test strip 200 from the timer system 27 and dip it into the urine sample. As soon as the user withdraws the dry (undipped) test strip 200 from the timer system 27, operation 336 is activated by the timer system 27 which is in electronic communication with the computation system 62. The timer system 27 can detect the withdrawal of the test strip 200. Operation 336 begins a software timer, and also displays a visual countdown timer on the screen for the user to see, where the software timer and on-screen timer counts down from 30 seconds to 0 seconds or counts down from any other specific time needed for a specific test strip 200. Next, Prompt User 338 guides the user to load the dipped test strip 200 into the test strip holder 30 (Tray) and then to insert the test strip holder 30 (Tray) into the aperture 28 (Device) before the on-screen timer reaches 0 seconds. Next, operation 340 captures an image using the camera module 82, where such image capture takes place 30 seconds after the software timer began or takes place by any other specific time needed for a specific test strip 200. Next, operation 342 processes the captured image by performing computer vision processing which may include image processing, feature recognition, and/or pattern recognition as appropriate. This computer vision processing will determine if the following errors have occurred: (a) test strip holder 30 not inserted within allowable time period (determined together with information from the timer system 27); (b) test strip holder 30 not inserted properly into aperture 28 (i.e. partial insertion); (c) test strip 200 not inserted properly into test strip holder 30 (either misalignment, poor orientation, or partial insertion); (d) Anomalous results measured from test strip 200 (indication of possible contamination by dirt or obstruction on reagent pads 204, 206, 212 or interfering analytes); and (e) test strip 200 not fully immersed in urine sample (known since reagent pads 204, 206 on a wet test strip 200 are noticeably different in color from dry (undipped) test strip 200). Other error checks with computer vision are also possible. If a problem is detected, operation Message to User 344 will inform the user that a problem has occurred, and that the test is invalid. It will also inform the user the type of problem that was detected, and suggest a possible remedy, and next provide a Message to User 346 to try the test again. The software will the return the user to the Main Application Screen 316.

If no problem is detected during operation 342, operation Message to User 350 will inform the user that the test is in progress, and for the user to wait while operation 352 takes place, where the screen shows a visual countdown timer for the user to see, where the visual timer counts down from 130 seconds to 0 seconds or counts down from any other specific time needed for a specific test strip 200. Operation 352 begins a software timer that counts down from 130 seconds to 0 seconds or counts down from any other specific time needed for a specific test strip 200. Depending on the reagent pads 204 present on a test strip 200, different reagent pads 204 need to be imaged at different times after being immersed in the urine sample, due to different types of chemistry used to create color changes in response to analytes in urine. Imaging within a correct time range is important for accuracy of the colorimetric result. As such, during the 130 second interval, the computation system 62 will control the camera module 82 to take several images of the test strip 200 within specific time ranges, for example at 44 to 46 seconds, at 59 to 61 seconds, at 129 to 131 seconds, and so forth. Within each of these time ranges, several images of the test strip 200 will be taken, where each image is illuminated by a different frequency of LED light. The device 10 employs an illumination PCB 50 which has multiple LEDs, which are RGB LEDs 52, white LEDs 54, orange LEDs 55, infrared LEDs 56, and ultraviolet LEDs 57. For example, during the specific time range of 44 to 46 seconds, an image is taken under only Red LED illumination, an image is taken under only Green LED illumination, an image is taken under only Blue LED illumination, an image is taken under only White LED illumination, an image is taken under only Orange LED illumination, an image is taken under only Infrared LED illumination, and an image is taken under only UV LED illumination. Similar imaging is done at other specific time ranges. Depending on the chemistry of a particular reagent pad 204, different images taken under different frequencies of light are used in combination for colorimetric analysis of that reagent pad 204. After operation 352 is completed, operation 354 processes the captured images by performing computer vision processing which may include image processing, feature recognition, and/or pattern recognition as appropriate. This computer vision processing will be followed with a calibration process and a mapping process to provide colorimetric analysis and thereby provide results indicating the levels of analytes found in the urine sample. The software will then determine if those results may indicate problems with the test as follows: (a) Specific gravity results too low, which would invalidate the test; (b) Specific gravity results too high, which would invalidate the test; (c) High levels of albumin are detected, which would invalidate the leukocyte test; (d) High levels of vitamin C (Ascorbic Acid), which would invalidate the test for leukocyte and nitrite; and (e) Colorimetric result of any particular reagent pad 204 that is far beyond any possible low range or high range for human urine, indicating a problem with the sample. Other error checks with computer vision are also possible. If a problem is detected, operation Message to User 344 will inform the user that a problem has occurred, and that the test is invalid. It will also inform the user the type of problem that was detected, and suggest a possible remedy, and next provide a Message to User 346 to try the test again. The software will the return the user to the Main Application Screen 316.

If no problem is detected during operation 354, operation Message to User 356 will inform the user that the test is completed. It will display the test results to the user in either text or visual format and allow the user to add an optional text note regarding that particular test. The operation will then save the results by appending them to the test results data-log for that particular user. The software will the return the user to the Main Application Screen 316.

The device 10 is capable of four different calibration operations, which are performed at various times. Given the variability of electronic component properties (for example variations in LED luminous output as obtained from LED suppliers vs a standard current), and the variability in camera module 82 response, the raw-data readings obtained from various uncalibrated devices 10, may vary. Therefore, calibration processes are done. Some of these calibration operations use standard targets, which are made of standard materials which have a very specific and well-known colorimetric response to the various light sources provided by the illumination PCB 50. One such standard target is the Standard Calibration Target 220, which is a thick PTFE (Polytetrafluoroethylene) strip 220 with matte finish, in the form factor of a test strip 200. The PTFE strip 220 is uniformly white along its length and is imaged at locations corresponding to the locations of the reagent pads 204, 206. This is performed by the user during the Settings and Data Management 324 operation, at sub-operation Calibration Menu. Another such standard target is the YouRStrip™ Standard Target 212, which is an additional pad that can be added to each test strip 200, 210, consisting of a non-reactive white polymer, that exhibits no color change when either wet or dry. This non-reactive white polymer has a very specific and well-known colorimetric response to the various light sources provided by the illumination PCB 50. This calibration would be performed during each test during the Read Test Strip Function 318, at sub-operation 342, when using test strips 210 equipped with the YouRStrip Standard Target 212. There are four different calibrations that are done, as follows: (1) Factory Baseline Calibration: A statistically significant number of devices 10 are selected at random from the manufactured batch of devices 10 at the factory. A Standard Calibration Target 220 is loaded into each of these devices 10, where the Standard Calibration Target 220 is imaged, and that image is processed for colorimetric response. The CMOS camera measurement data captured from these devices 10, is then used to create a "Global_Average_Value" data matrix, which serves as a baseline reference value for all devices 10 manufactured in that batch; (2) Aqua Calibration: Each manufactured device 10 is calibrated at the factory prior to being shipped to home users. A Standard Calibration Target 220 is loaded into each device 10 and imaged, which provides a CMOS camera measurement used to create a "Device_Average_Value" data matrix. This matrix is in turn compared to the "Global_Average_Value" data matrix, to create two new matrices: (a) a shift-matrix, and (b) a normalization-matrix; (3) Result Data Calibration: This step is done every time the device 10 reads a test strip 200, during the Read Test Strip Function 318. This step ensures consistent results across any device 10 when reading the test strip 200, when that test strip 200 is subjected to a standard/known concentration urine sample. Therefore, any one of the tens-of-thousands of devices 10 would produce the same result data (within a margin of error of 5%) for a standard/known urine sample. This works as follows: When the device 10 performs the Read Test Strip Function 318, sub-operation 354, it first obtains a raw data result from a test strip 200. The shift-matrix provides an offset correction to the raw-data values (compared to Baseline Calibration averages). The normalization-matrix provides a scale-correction to the "shifted" raw-data values at each of the 8-12 reagent pad 204 locations read from a test strip 200. Together, the shift and normalization of the raw-data values, create a calibrated-data value matrix for each test strip 200 that is read. In a later processing step in sub-operation 354, the calibrated-data values are "mapped" against known response values of standard/known samples of urine analytes, to provide a test result data matrix. The test result data matrix is stored in a user data file called the test result data-log, where test result data-log is available for the user to review in a number of ways, using the View Results: Plotting and Graphing 320 operation; and (4) Strip Calibration: for cases where the test strip 210 contains a YouRStrip Standard Target 212, the test strip 210 is checked each time a test is run. Since this is a non-reactive pad 212, the GUI App checks for consistency with respect to the expected value based on the Baseline Calibration. This is an independent quality check done every time a test strip 210 is read.

Example 1

The system is used for asymptomatic (i.e. healthy people) to monitor their body chemistry. In particular for lay-users such as athletes, fitness-orientated users, bodybuilders, health minded individuals and other users partake in nutritional programs, for example, but not limited to low-carb high-protein programs, exercise programs to develop muscle tone and reduce fat, as well as programs to improve their overall health.

The software will provide information on what is "normally expected urine analyte levels" for the user of a particular type of user. For example, an athlete will have analyte ranges in a typical range, and the system will inform the user that those are typical ranges. Such lay-users are able to purchase a multitude of protein-based supplements, meal replacements, or vitamins. The system allows the users to measure their levels of ketone, protein, specific gravity, pH, glucose, creatinine, calcium and other analytes in their urine. The specific gravity test allows a user to determine their level of hydration in addition to being an indicator of a valid or invalid test.

Alternatively, people on a low-carb high-protein diets will generally have urine analyte levels within specific ranges. Therefore, the software will provide such interpretive information, so that when users see their own individual results when using the system, they will have some interpretive/context information. In general, specific lay-user groups doing specific activities will be provided interpretive information on typical urine analyte levels for people doing those activities. Such information will be stored in the memory and provided by the system.

Others are interested in their pH balance—where our bodies have natural acidity affecting our pH balance. A pH between 7 to 7.4 is an ideal range for the body to function properly. This is important to the lay-user interested in their health because acidity lowers the body's ability to absorb nutrients found in food.

Data-logging measurements of urine analytes is a core function of the system. Time based data-logging is important, because different users will have different baseline levels, and hence the device and system will allow such health and fitness orientated users to monitor changes in their levels.

Example 2

Consumer interest in daily or weekly logging of body metrics data exists today due to the increasing exposure to other data-logging devices such as heart rate wrist monitors, blood pressure monitors, body mass scales, and body fat measurement devices. Such daily or weekly monitoring is not suitable for the medical system for such purposes and would be cost prohibitive for the medical system for such a routine frequency. The system provides an at-home solution for the lay-user.

Example 3

The system is used for symptomatic (i.e. unhealthy people) to monitor their body chemistry. This may include applications such as, but not limited to, sexually transmitted disease, recreational drug use, illicit drug use, urinary tract infection, monitoring kidney function, monitoring liver function, dehydration, and monitoring glucose. Specific examples of analytes of interest and the rationale behind the interest include, but are not limited to:

The microalbumin:creatinine ratio in urine is used to detect damage to kidneys and chronic kidney dysfunction. It provides more diagnostic information on kidney function when combined with the protein:creatinine ratio than the protein:creatinine ratio alone.

There are several reasons that users may be interested in their urinary calcium. High urinary calcium levels can affect urinary tract health by increasing the risk of kidney stones and calcium deposits forming in the kidney. High calcium levels in urine can indicate excessive calcium intake or calcium loss from bone. Low levels can be indications of insufficient calcium or sodium intake.

Female users interested in their reproductive health could benefit from measuring their levels of human chorionic gonadotropin, lutenizing hormone, follicle stimulating hormone and estrogen. Levels of these hormones fluctuate significantly during the menstrual cycle and pregnancy. Being aware of fluctuations in these hormones, may help users adapt or evaluate changes in body chemistry.

While example embodiments have been described in connection with what is presently considered to be an example of a possible most practical and/or suitable embodiment, it is to be understood that the descriptions are not to be limited to the disclosed embodiments, but on the contrary, is intended to cover various modifications and equivalent arrangements included within the spirit and scope of the example embodiment. Those skilled in the art will recognize, or be able to ascertain using no more than routine experimentation, many equivalents to the specific example embodiments specifically described herein. Such equivalents are intended to be encompassed in the scope of the claims, if appended hereto or subsequently filed.

The invention claimed is:

1. A urinalysis device comprising:
   a housing defining an interior and an aperture extending between an ambient environment and the interior;
   a slide extending from the aperture into the interior;
   a test strip holder removably engageable with the slide;
   a plurality of light emitting diodes (LEDs) in the housing;
   a camera module in the housing and operable with the plurality of LEDs to capture images of a test strip located in the test strip holder when engaged with the slide;
   a timer system operable to start a timer when the test strip holder is disengaged from the slide; and
   a computation system operable with the plurality of LEDs, the camera module, and the timer system to—
   after the test strip holder has been disengaged from the slide, the test strip has been located in the test strip holder, and the test strip holder has been re engaged with the slide:
   read the images of the test strip;
   determine an elapsed time between when the test strip holder was disengaged from the slide and then reengaged with the slide; and
   determine whether the elapsed time is within a time limit.

2. The device of claim 1, wherein the plurality of LEDs comprise a white LED and one or more of:
   an orange LED;
   an infrared LED;
   a red-blue-green (RBG) LED; and
   an ultraviolet (UV) LED.

3. The device of claim 1, wherein:
   the slide comprises a distal stop and a pair of rails extending outwardly from an interior surface of the housing; and
   the test strip holder is slidably engageable with the slide when located between the pair of rails.

4. The device of claim 3, wherein:
   the plurality of LEDs and the camera module are directed to an illumination and detection zone in the interior of the housing; and
   the pair of rails are operable with the distal stop to locate the test strip holder in the illumination and detection zone.

5. The device of claim 1, wherein the test strip holder comprises a base and a pair of sides extending outwardly from the base to define a slot operable to locate the test strip in the test strip holder.

6. The device of claim 1, wherein the camera module is operable to detect when the test strip holder has been disengaged from the slide by continuously recording and processing the images of the test strip in the test strip holder.

7. The device of claim 1, wherein the timer system comprises one or more of:
   a computational timer;
   a photo interrupter operable to detect the test strip holder with a light beam affected by the test strip holder when engaged with the slide;
   a proximity detector operable to detect the test strip holder by measuring a light reflected from the test strip holder when engaged with the slide; and
   a switch actuated by the test strip holder when engaged with the slide.

8. The device of claim 1, wherein the camera module is operable to conduct error checks for one or more of:
   correct insertion of the test strip holder;
   correct insertion of the test strip;
   dirt or obstruction on the test strip; and
   correct wetting of the test strip.

9. The device of claim 8, wherein the computation system is operable to generate an error report based on the error checks.

10. The device of claim 9, comprising a touchscreen on the housing and operable to display the error report.

11. The device of claim 1, wherein, after the test strip holder has been reengaged with the slide, if the elapsed time indicated by the timer is within the time limit, then:
    the camera module captures the images of the test strip; and
    the computation system determines urinalysis results by reading the images of the test strip.

12. The device of claim 11, comprising a touchscreen on the housing and operable to display a graphic of the urinalysis results.

13. The device of claim 12, wherein the computation system is operable to the store the urinalysis results in a historical data log.

14. The device of claim 13, wherein the computation system is operable to upload the urinalysis results to an internet server.

15. The device of claim 1, wherein the computation system comprises a processor and a memory in electronic communication with the plurality of LEDs, the camera module, the timer system, and an internet server.

16. The device of claim 1, wherein the computation system does not store urinalysis results based on the images of the test strip if the elapsed time is outside of the time limit to prevent inaccurate results caused by reading the test strip outside of the time limit.

17. The device of claim 1, comprising the test strip.

18. The device of claim 17, wherein:
    the test strip comprises a plurality of absorbent reagent pads;
    the plurality of absorbent reagent pads comprise a blank non-reactive pad that does not undergo a color change after being wetted with urine; and
    the camera module is operable to calibrate the plurality of LEDs by illuminating the blank non-reactive pad.

19. The device of claim 18, wherein:
    the plurality of LEDs comprise an ultraviolet (UV) LED positioned to illuminate the blank non-reactive pad when the test strip holder is engaged with the slide; and
    the camera module is operable with the UV LED to detect nucleic acids in the urine by illuminating the blank non-reactive pad with a UV light output from the UV LED.

20. The device of claim 17, wherein:
the test strip comprises a plurality of absorbent reagent pads;
the plurality of absorbent reagent pads comprise a timing reagent pad having a color change after being wetted with urine, the color change being caused by water in the urine and not affected by other analytes present in the urine; and
the computation system is operable to read the images of the test strip and determine the elapsed time by resolving the slow reaction color change into time steps.

21. The device of claim 20, wherein the slow reaction color change lasts at least sixty (60) seconds and the time steps are at least one (1) second.

22. The device of claim 1, where the camera module comprises one or more of:
a complementary metal oxide semiconductor camera;
a charge coupled device camera;
a matrix of photosensors;
a color camera;
a monochromatic camera;
a color filter array; and
a filter mosaic.

23. A method of operating the urinalysis device of claim 1, the method comprising:
detecting, with the camera module or the timer system, when the test strip holder is disengaged from the slide; and
starting, with the timer system, the timer after the detecting step.

24. The method of claim 23, wherein the detecting step comprises one or more of:
continuously recording and processing the images of the test strip;
determining whether a light beam has been affected by the test strip holder;
measuring a light reflected from the test strip holder;
actuating a switch with the test strip holder; and
illuminating a portion of the test strip.

25. A method of operating the urinalysis device of claim 1, the method comprising:
detecting, with the camera module, when the test strip holder has been disengaged from the slide;
starting, with the timer system, the timer relative to the detecting step;
detecting, with the camera module, when the test strip holder has been re-engaged with the slide; and
recording, with the computation system, the elapsed time indicated by the timer when the test strip holder is detected as being re-engaged with the slide.

26. The method of claim 25, comprising:
determining, with the computation system, whether the elapsed time exceeds the time limit; and
if the elapsed time is less than the time limit, then:
capturing, with the camera module, the images of the test strip in the test strip holder after being re-engaged with the slide; and
analyzing, with the computation system, the images of the test strip.

27. A method of operating the urinalysis device of claim 1, the method comprising:
conducting, with the camera module, error checks for one or more of:
correct insertion of the test strip holder;
correct insertion of the test strip;
dirt or obstruction on the test strip; and
correct wetting of the test strip.

28. The method of claim 27, wherein the device comprises a touchscreen and the method comprises displaying, with the touchscreen, one or more of:
instructions for performing testing steps;
an error report based on the error checks;
a countdown timer after detecting that the test strip holder has been disengaged from the slide; and
a graphic of urinalysis results.

29. The method of claim 28, wherein displaying the instructions for performing testing steps comprises displaying, with the touchscreen, instructions for one or more of:
selecting the test strip;
wetting the test strip with urine to provide a wetted test strip;
inserting the wetted test strip into the test strip holder; and
inserting the test strip holder into the housing.

30. A method of operating the urinalysis device of claim 1, wherein the urinalysis device comprises a touchscreen, the method comprises operations performable by a user with the touchscreen, and the operations comprise one or more of:
displaying, with the touchscreen, a set of questions;
receiving, with the touchscreen, answers from the user;
determining, with the computation system, based on the answers, one or more of:
an identity of the user;
whether the user is qualified to operate the urinalysis device; and
obtaining, with the touchscreen, a declaration from the user.

31. A urinalysis system comprising:
a test strip comprising a timing reagent pad having a color change after being wetted with urine; and
a urinalysis device comprising:
a housing defining an interior and an aperture extending between an ambient environment and the interior;
a slide extending from the aperture into the interior;
a test strip holder removably engageable with the slide;
a plurality of light emitting diodes (LEDs) in the housing;
a camera module in the housing and operable with the plurality of LEDs to capture images of the test strip located in the test strip holder holder when engaged with the slide;
a timer system operable to start a timer when the test strip holder is disengaged from the slide; and
a computation system operable with the plurality of LEDs, the camera module, and the timer system to — after the test strip holder has been disengaged from the slide, the test strip has been located in the test strip holder, and the test strip holder has been reengaged with slide:
read the images of the test strip; and
resolve the color change into time steps allowing for measurement of an elapsed time since the timing reagent pad was wetted with the urine.

* * * * *

UNITED STATES PATENT AND TRADEMARK OFFICE
CERTIFICATE OF CORRECTION

| | |
|---|---|
| PATENT NO. | : 11,585,804 B2 |
| APPLICATION NO. | : 16/166052 |
| DATED | : February 21, 2023 |
| INVENTOR(S) | : Nikolai Dechev and Teodora Dechev |

Page 1 of 1

It is certified that error appears in the above-identified patent and that said Letters Patent is hereby corrected as shown below:

In the Claims

Column 20, Line 37, of Claim 13 reading:
"system is operable to the store the urinalysis results in a"
Should read:
--system is operable to store the urinalysis results in a--

Column 21, Line 11, of Claim 20 reading:
"ing the slow reaction color change into time steps."
Should read:
--ing the color change into time steps.--

Column 21, Line 12, of Claim 21 reading:
"The device of claim 20, wherein the slow reaction"
Should read:
--The device of claim 20, wherein the--

Column 22, Line 48, of Claim 31 reading:
"located in the test strip holder holder when engaged"
Should read:
--located in the test strip holder when engaged--

Signed and Sealed this
Thirteenth Day of May, 2025

Coke Morgan Stewart
*Acting Director of the United States Patent and Trademark Office*